(12) United States Patent
Flohr et al.

(10) Patent No.: US 9,186,114 B2
(45) Date of Patent: Nov. 17, 2015

(54) METHOD FOR PRODUCING A NOISE-REDUCED CT IMAGE DATA RECORD, COMPUTER SYSTEM, AND CT SYSTEM

(71) Applicant: Siemens Aktiengesellschaft, Munich (DE)

(72) Inventors: Thomas Flohr, Uehlfeld (DE);
Bernhard Krauβ, Burgthann (DE);
Rainer Raupach, Heroldsbach (DE);
Bernhard Schmidt, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 562 days.

(21) Appl. No.: 13/628,498

(22) Filed: Sep. 27, 2012

(65) Prior Publication Data
US 2013/0083989 A1 Apr. 4, 2013

(30) Foreign Application Priority Data
Sep. 29, 2011 (DE) .......................... 10 2011 083 727

(51) Int. Cl.
*G06K 9/00* (2006.01)
*A61B 6/03* (2006.01)
*A61B 6/00* (2006.01)

(52) U.S. Cl.
CPC . *A61B 6/03* (2013.01); *A61B 6/032* (2013.01);
*A61B 6/4014* (2013.01); *A61B 6/482* (2013.01); *A61B 6/541* (2013.01)

(58) Field of Classification Search
None
See application file for complete search history.

(56) References Cited

U.S. PATENT DOCUMENTS

| 2007/0092056 A1 | 4/2007 | Flohr et al. |
| 2009/0147919 A1 | 6/2009 | Goto et al. |
| 2010/0092060 A1 | 4/2010 | Bruder et al. |

FOREIGN PATENT DOCUMENTS

| CN | 101023875 | | 8/2007 |
| CN | 101175440 | A | 6/2009 |
| DE | 102005049586 | A1 | 4/2007 |
| DE | 102008051043 | B3 | 2/2010 |
| DE | 102008045633 | A1 | 3/2010 |
| DE | 102009015772 | A1 | 8/2010 |

*Primary Examiner* — Vikkram Bali
(74) *Attorney, Agent, or Firm* — Harness, Dickey & Pierce (57) ABSTRACT

A method is disclosed for producing a noise-reduced CT image data record by frequency band breakdown, a computer system for carrying out the method, and a CT system (1) with such a computer system. In an embodiment of the method, several linear-combined mixed image data records

$$\left(M_m = c_{0,m} + \sum_i c_{i,m} \cdot X_i\right)$$

are produced from several simultaneously-recorded energy spectrum-specific CT image data records ($X_i$); a frequency band breakdown of the mixed image data records ($M_m$) takes place into a first lowest frequency band ($F_0$) and several higher frequency bands; and a result image data record $$\left(E = \sum_{j,m} g_{j,m}(r) \cdot F_j \cdot M_m\right)$$

is calculated, wherein each mixed image data record ($M_m$) is multiplied with precisely one filter and with a location-dependent function ($g_{j,m}(r)$) and is thereby totaled, and wherein $g_{0,0}(r)=1$.

17 Claims, 4 Drawing Sheets

METHOD FOR PRODUCING A NOISE-REDUCED CT IMAGE DATA RECORD, COMPUTER SYSTEM, AND CT SYSTEM

PRIORITY STATEMENT

The present application hereby claims priority under 35 U.S.C. §119 to German patent application number DE 10 2011 083 727.2 filed Sep. 29, 2011, the entire contents of which are hereby incorporated herein by reference.

FIELD

At least one embodiment of the invention generally relates to a method for producing a noise-reduced CT image data record by frequency band breakdown, a computer system for carrying out embodiments of the method, and/or a CT system with such a computer system.

BACKGROUND

It is generally known that, with the aid of multi-energy CT systems it is possible to record simultaneously CT image data records of an object with different X-ray spectra. As a rule, the attempt is made to calculate from these CT image data records a single image with the desired information, such as a CT image which corresponds to a mono-energy spectrum, or only represents the contrast agent distribution in the scanned object. To this end, a linear-mixed image $$M_m = c_{0,m} + \sum_i c_{i,m} \cdot X_i$$

can be produced, wherein $X_i$ designates the den CT image data record for the i-th X-ray spectrum, the coefficients are selected such as to achieve a special image impression, and m=0. Unfortunately, the noise in such linear combinations can increase substantially in comparison with a noise-optimized mixed image.

In the prior art there are many possibilities known for reducing the noise of the mixed images which are produced. For example, a linear filter in the form of a low-pass filter can be used, wherein, however, the spatial resolution is sharply reduced. As an alternative, non-linear filters are used, but, with complex structures in the object represented, the problem arises of distinguishing fine structures from the noise.

SUMMARY

At least one embodiment of the invention provides an improved method for producing a noise-reduced CT image data record from several CT image data records, recorded with different X-ray energy spectra.

Advantageous developments of the invention form the subject matter of the subordinated claims.

A method is proposed, in at least one embodiment, for producing a noise-reduced CT mixed image data record as a result image data record which comprises the method steps indicated in the following enumeration:

Simultaneous recording of several energy spectrum-specific CT image data records $X_i$ with different X-ray energy spectra $R_i$ or received from several simultaneously recorded energy spectrum-specific CT image data records $X_i$ with different X-ray energy spectra $R_i$, Calculation of several linear-mixed mixed image data records $$M_m = c_{1,m} + \sum_i c_{i,m} \cdot X_i,$$

from the energy spectrum-specific CT image data records $X_i$

Frequency band breakdown of the mixed image data records $M_m$ into a first lowest frequency band, produced with a low-pass filter $F_0$, and several higher frequency bands, produced by other filters $F_j$, wherein all the other filters $F_j$ block the frequency zero and the sum $$\sum_j F_j(f) = 1$$

over all the filters is standardized for all frequencies f, and

Calculation of a result image data record $$E = \sum_{j,m} g_{j,m}(r) \cdot F_j \cdot M_m$$

in that each mixed image data record $M_m$ is multiplied by precisely one filter and with a location-dependent function $g_{j,m}(r)$ and thereby totaled, wherein $g_{0,0}(r)=13$.

As well as the method according to embodiments of the invention, the inventors also propose a computer system, which comprises a memory for the storing of a computer program to be carried out during operation, wherein the computer program carries out the method steps in accordance with one of the preceding method embodiments.

In addition to this, an embodiment of the invention also includes a CT system for the production of several linear mixed image data records, mixed from the energy spectrum-specific CT image data records, with a computer system such as described heretofore.

BRIEF DESCRIPTION OF THE DRAWINGS

The invention is described hereinafter in greater detail on the basis of example embodiments and with the aid of the Figures, wherein only those features are represented which are necessary for the understanding of the invention. The following reference numbers are used: 1: Dual-source/Dual-energy CT system; 2: First X-ray tubes; 3: First detector; 4: Second X-ray tubes; 5: Second detector; 6: Gantry housing; 7: Patient; 8: Examination couch: 9: System axis; 10: Control and calculation unit; 11: Contrast medium applicator; 12: Control and data line; 13: ECG lead; 14: Memory; 15: Computer programs; E: Result image; F0: Low-pass filter; F1: High-pass filter; Fi: Filter operations; M0: Image; M1: Mixed image; Mm: Mixed image data records; Ri: X-ray energy spectrum; S1: Determination of C-image data records; S2: Formation of mixed image data records; S3: Breakdown of the mixed image data records into different frequency bands; S4: Determination of the location-dependent function; S5: Calculation of the mixed image; V(r): Voxel; V(r±Δr): Voxels in the adjacent region with maximum distance interval Δr.

Specifically, the following are shown.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

A method is proposed, in at least one embodiment, for producing a noise-reduced CT mixed image data record as a result image data record which comprises the method steps indicated in the following enumeration:

Simultaneous recording of several energy spectrum-specific CT image data records $X_i$ with different X-ray energy spectra $R_i$ or received from several simultaneously recorded energy spectrum-specific CT image data records $X_i$ with different X-ray energy spectra $R_i$, Calculation of several linear-mixed mixed image data records $$M_m = c_{1,m} + \sum_i c_{i,m} \cdot X_i,$$

from the energy spectrum-specific CT image data records $X_i$

Frequency band breakdown of the mixed image data records $M_m$ into a first lowest frequency band, produced with a low-pass filter $F_0$, and several higher frequency bands, produced by other filters $F_j$, wherein all the other filters $F_j$ block the frequency zero and the sum $$\sum_j F_j(f) = 1$$

over all the filters is standardized for all frequencies f, and
Calculation of a result image data record $$E = \sum_{j,m} g_{j,m}(r) \cdot F_j \cdot M_m$$

in that each mixed image data record $M_m$ is multiplied by precisely one filter and with a location-dependent function $g_{j,m}(r)$ and thereby totaled, wherein $g_{0,0}(r)=1$.

The inventor has recognized the following:

It is possible to produce, from several energy spectrum-specific CT image data records $X_i$, based on different X-ray energy spectra $R_i$, several different mixed images according to $$M_m = c_{0,m} + \sum_i c_{i,m} \cdot X_i,$$

and to carry out a frequency band breakdown on these mixed images. In this situation, the first frequency band corresponds to a low-pass filter $F_0$, which contains the frequency f=0 in full strength. The other filters $F_j(f)$ are designed in such a way that $$\sum_j F_j(f) = 1$$

for all frequencies. This means that all the other filters block the frequency. It is now possible to form the sum over m mixed images with $$\sum_{j,m} F_j \cdot M_m,$$

wherein on each mixed image $M_m$ the operator $F_j$ is applied, and the mixed images differ from one another at least in one coefficient $C_{i,m}$.

On the assumption that locally only two different materials are present which are mingled microscopically or macroscopically, it is now possible to define functions $g_{j,m}(r)$, which ensure that at the location r a CT image data record is produced, which, apart from the noise, is identical to the original mixed image $M_0$. The following applies accordingly:

$$M_0 \approx \sum_{j,m} g_{j,m}(r) \cdot F_j \cdot M_m = E,$$

wherein $g_{0,0}(r)=1$.

This method is useful in particular when the CT image data record $M_0$ exhibits a relatively high noise in comparison with a noise-optimized mixed image, and, as well as this, the same high-frequency structures are visible in both images, wherein they differ from one another only in their amplitude. In order to avoid discontinuities from occurring in the image by way of the functions $g_{j,m}(r)$, care must be taken to ensure that the values of the scaling functions $g_{j,m}(r)$ do not vary too much spatially.

In accordance with this recognition, the inventor proposes a method for producing a noise-reduced CT mixed image data record as a result image data record which comprises the method steps indicated in the following enumeration:

Simultaneous recording of several energy spectrum-specific CT image data records $X_i$ with different X-ray energy spectra $R_i$ or received from several simultaneously recorded energy spectrum-specific CT image data records $X_i$ with different X-ray energy spectra $R_i$, Calculation of several linear-mixed mixed image data records $$M_m = c_{1,m} + \sum_i c_{i,m} \cdot X_i,$$

from the energy spectrum-specific CT image data records $X_i$

Frequency band breakdown of the mixed image data records $M_m$ into a first lowest frequency band, produced with a low-pass filter $F_0$, and several higher frequency bands, produced by other filters $F_j$, wherein all the other filters $F_j$ block the frequency zero and the sum $$\sum_j F_j(f) = 1$$

over all the filters is standardized for all frequencies f, and

Calculation of a result image data record $$E = \sum_{j,m} g_{j,m}(r) \cdot F_j \cdot M_m$$

in that each mixed image data record $M_m$ is multiplied by precisely one filter $F_j$ and with a location-dependent function $g_{j,m}(r)$ and thereby totaled, wherein $g_{0,0}(r)=1$.

Attention is drawn to the fact that, in the examples given here of the nomenclature and formulae, the counting of the indices begins in each case at 0, and the formulae given represent only examples of calculations.

With such a method, a noise reduction is now possible, with which the edges are approximately retained, wherein the image quality is potentially better than with non-linear methods, which assess the local geometry.

In an embodiment of the method according to the invention, it is proposed that the location-dependent function $g_{j,m}(r)$ is formulated in such a way that the local areas of the skin surface exhibit a different constant value than the inner regions of the patient.

As an alternative, it is also possible to determine the location-dependent function $g_{j,m}(r)$ locally from a statistical evaluation of the surroundings of each voxel V(r) at the location r. This can be done to advantage in that:

A CT image data record $X_1$ is selected,

From this CT image data record $X_1$ moving via predefined adjacent voxels V(r±Δr) of each voxel considered V(r) to the remaining CT image data records $X_i$, regression coefficients $k_i$ (=gradient of the regression lines) are calculated, which reveal the mutual dependency of the CT values of the adjacent voxels in each case of the CT image data records $X_i$ to the selected CT image data record $X_1$, A location-dependent scaling function $$h_m(r) = \frac{\sum_i c_{i,0} k_i}{\sum_i c_{i,m} k_i}$$

is determined,

From this, in turn, the location-dependent function $g_{j,m}(r) = w_{j,m}(r) \cdot h_m(r)$ is determined, wherein $$\sum_k w_{j,m} = 1$$

for all j, and

The result image data record is determined as the summation via the product from the location-dependent function with the filters and the mixed images to give $$E = \sum_{j,m} g_{j,m}(r) \cdot F_j \cdot M_m.$$

As the outcome, this corresponds to a different weighting of the mixed image data records used, wherein this weighting can also be carried out by the user of the method as required, in an adjustable manner, such that, for example, a homogenous noise impression is produced. In this situation, the scaling h can lead to the result image E fluctuating sharply in noise without a location-dependent w.

According to another embodiment variant of the method presented, the location-dependent function $g_{j,m}(r)$ can be determined by a location-dependent classification on the basis of the local CT values of the voxels. As an alternative, the location-dependent function $g_{j,m}(r)$ can also be determined by a classification of locally-determined materials, wherein the local materials are determined for preference by an inherently known method of material breakdown of CT image data records $X_i$ into at least two materials. In this respect, reference is made, by way of example, to the Patent Applications under the File References DE102008018245.1 and DE102005049586.9, the entire contents of each of which are incorporated herein by reference.

The energy spectrum-specific CT image data records $X_i$ can, for the method described here, be both two-dimensional sectional image data records as well as three-dimensional volume image data records.

For particular preference, two CT image data records $X_i$ of a dual-energy CT scan can be used as energy-specific CT image data records $X_i$.

The CT image data records $X_i$ can in each case derive directly from scanning with a mono-energy X-ray spectrum, or they can be calculated by image-based or raw data-based methods, making use of polychromatic spectra mixed image data records $X_i$, which in each case correspond to a scanning with a mono-energy X-ray spectrum.

As well as the method according to embodiments of the invention, the inventors also propose a computer system, which comprises a memory for the storing of a computer program to be carried out during operation, wherein the computer program carries out the method steps in accordance with one of the preceding method embodiments.

In addition to this, an embodiment of the invention also includes a CT system for the production of several linear mixed image data records, mixed from the energy spectrum-specific CT image data records, with a computer system such as described heretofore.

Figure 1:
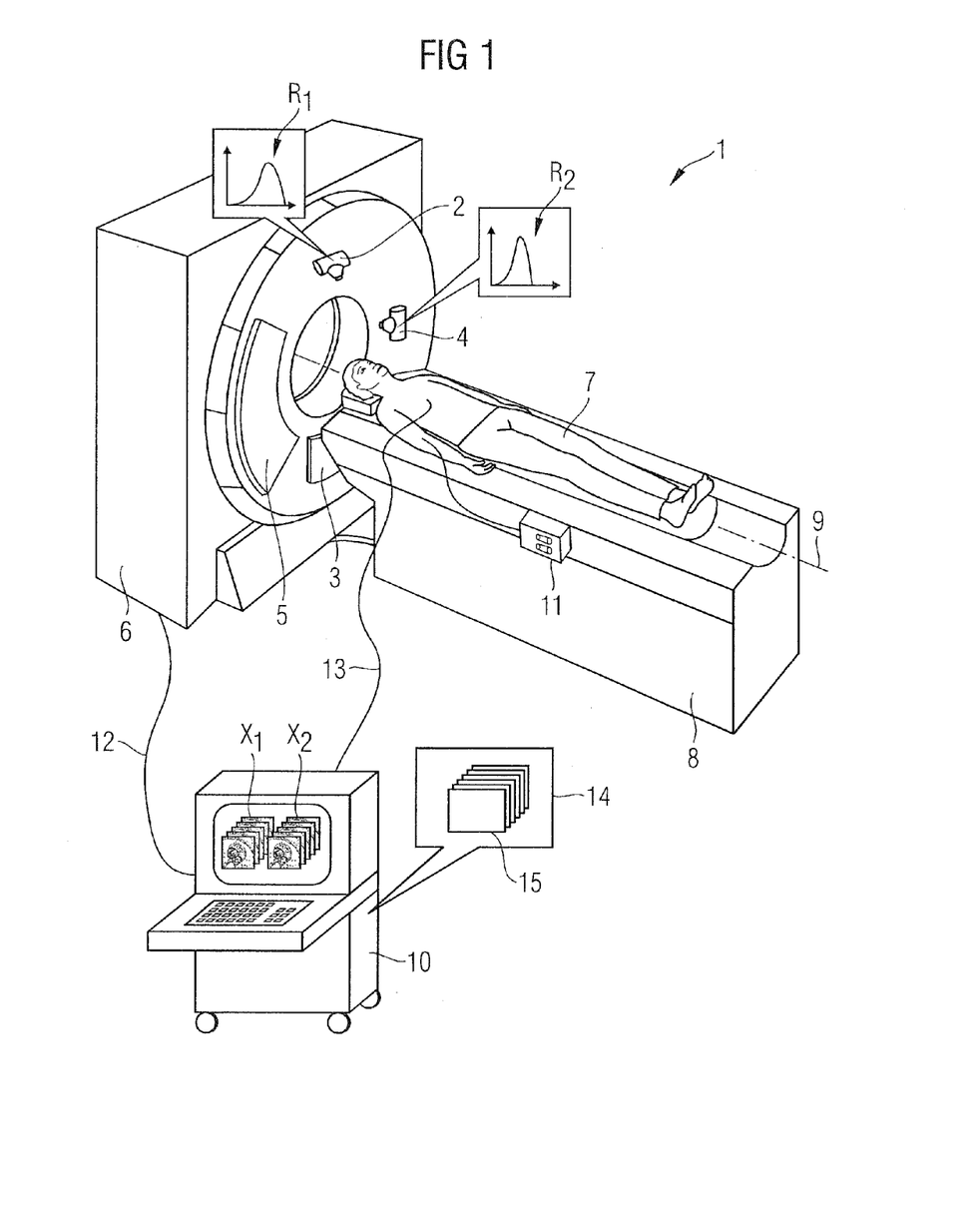
FIG. 1: Dual-source/Dual-energy CT-System.

FIG. 1 shows, by way of example, a dual-source/dual-energy CT system 1, with which the method according to an embodiment of the invention is carried out. The CT system 1 comprises a first radiator/detector system with an X-ray tube 2, and a detector 3 located opposite, wherein, with the first radiator/detector system 2, 3 absorption data items from a first X-ray energy spectrum R1 are recorded. The CT system 1 further comprises a second radiator/detector system, offset by 90°, for simultaneous scanning with a second X-ray energy spectrum R2, consisting of a second X-ray tube 4, with a second detector 5 located opposite. Both radiator/detector systems are located on a gantry, which is arranged in a gantry housing 6 and rotates about a system axis 9 during the scanning.

The patient 7 to be scanned is positioned on a slidable examination couch 8, which is pushed along the system axis 9 through the scanning field located in the gantry housing 6. In this situation, the weakening of X-ray radiation emitted by the X-ray tubes is measured by the detectors located opposite, and then, on the basis of the detector data acquired simultaneously by these radiator/detector systems, CT image data records $X_i$ of the scanned patient 7 are reconstructed from different X-ray spectra. As a supplement, the patient 7 can also be injected, with the aid of a contrast medium applicator 11, even during the scanning, with a contrast medium bolus, such that, for example, blood vessels become better identifiable. Furthermore, for cardio images, the cardiac activity is also measured with the aid of an ECG lead 13, and an ECG-actuated or triggered scanning is carried out.

The control of the CT system is effected with the aid of a control and calculation unit 10 via a control and data line 12, by which the raw data from the detectors 3 and 5 is transformed into control commands. Located in the memory 14 of the control and calculation unit 10 are computer programs 15, which, as well as the control of the CT system 1 and the reconstructions of the CT image data records, can also carry out the method according embodiments of the invention.

By way of supplement, it is pointed out that the method can also be carried out on a computer system which stands separately from the CT system, as soon as this computer system has been provided with the corresponding CT image data records or also the raw data for the independent reconstruction of the CT image data records.

Taking as a basis CT image data records which are produced with the dual-energy CT system 1 described in FIG. 1, or another inherently-known design of a CT system, such as a single-source CT-system with energy-releasing detector, which produces two CT image data records on the basis of different X-ray energies, it is possible, for example, for mixed images M0 to be calculated, with:

$$M_0 = c_{0,0} + \sum_i c_{i,0} \cdot X_i.$$

As a rule, the image M0 is calculated in order to fulfill a special diagnostic purpose, such as the subtraction of contrast agent from the image.

In order to remove the noise from the image M0, typically, by way of filter operators F0 and F1 a breakdown into two frequency bands is carried out, wherein F0 designates a low-pass filter and F1 designates a high-pass filter.

The mixed image $$M_1 = c_{0,1} + \sum_i c_{i,1} X_i$$

can in this situation be determined, for example, such that it is the mixed image with the lowest noise, on the condition that $c0,1=0$ and $$\sum_i c_{i,1} = 1.$$

This corresponds to a standard CT image, in which air lies at −1000 HU, water at 0 HU, and which has the lowest noise. Naturally, other mixed images M1 can also be used, as long as this allows for a noise reduction to be achieved in the final result.

It is now possible to eliminate noise from the image M1 if it is known how the image contrasts in the CT image data records $X_i$ are correlated with one another. Since it can be assumed locally that in each case only two materials of constant density and composition mix with one another, it is known that the CT image data records $X_i$ are correlated in the surroundings of a point r, and $X_i(r) \approx k_i X_1(r) + t_i$, applies, with $k1=1$ and $t1=0$, wherein $k_i$ represents the correlation coefficients, i.e. the gradient of the regression lines.

It is therefore possible to determine the coefficients $k_i$, for example by a linear regression of the CT values in the image data record X1 and the image data record $X_i$ in a vicinity of the point r. In principle it is also possible to use other criteria, such as, for example:

a—A classification on the basis of the CT values in an image data record, e.g. M0, wherein, if the CT values of the voxels are in the vicinity of a voxel being observed ←500 HU, in other words if they define air, then all $k_i$ are set to be equal to 1, and otherwise there applies: $k_i=k_{i,0}$ with $k_{i,0}$=constant.

b—A classification on the basis of known materials in the vicinity (e.g. from the recognition of a material breakdown of the dual-energy CT image data record present), wherein $k_i=k_{i,B}$ with $k_{i,B}$=constant, if the adjacent voxels indicate the presence of bones and $k_i=k_{i,I}$ with $k_{i,I}$=constant, if iodine is in the vicinity.

In regions in which a linear regression does not provide any reliable results, i.e. with a low correlations coefficient, the $k_i$ can be calculated by a suitable interpolation of the adjacent voxel.

It is then known that in the frequency band F1 the images M0 and M1 differ locally only by the factor $$g_1(r) = \frac{\sum_i c_{i,0} k_i}{\sum_i c_{i,1} k_i}$$

There accordingly applies: $[F_1 \cdot M_0](r) \approx [F_1 \cdot M_1](r) \times g_1(r)$.

The following can therefore be written:

$$M_0 \approx [F_0 \cdot M_0](r) + w(r) \cdot [F_1 \cdot M_0](r) + (1-w(r)) \cdot [F_1 \cdot M_1](r) \cdot g_1(r),$$

wherein the weight w(r) is set in such a way that a special noise impression is produced, e.g. approximately constant noise everywhere in the image. As an alternative, w=0 can be selected, such that the upper frequency band derives only from the image M1. Accordingly, a breakdown into more than two frequency bands is also possible.

The CT image data records Xi can also be "mono-energetic" image data records, i.e. CT images with which attempts are made, on the basis of the multi-energy CT measured data, image-based or raw data-based, to achieve the image impression of a CT image which was recorded with only a single photon energy. Corresponding methods are generally known. As well as this, it is also possible, on the CT image data records Xi for a beam hardness increase correction, iterative, for example, to have already taken place.

Figure 2:
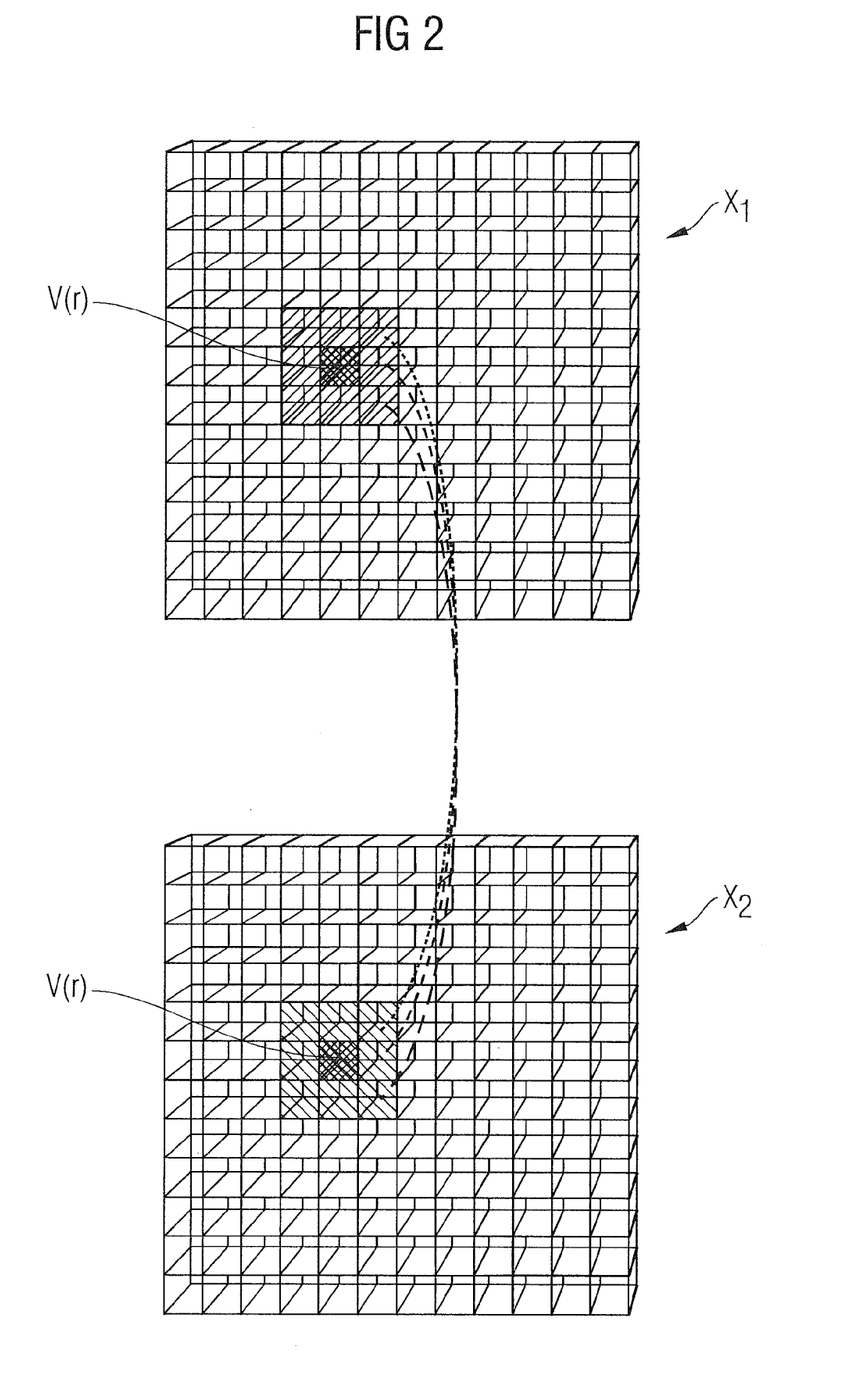
FIG. 2: Two diagrammatically-represented CT image data records for the correlation consideration.

For a better understanding of the correlation consideration, shown in FIG. 2 are two diagrammatically-represented CT image data records X1 and X2, including in each case a plurality of cubic voxels. A V(r) voxel considered in each case is marked in both CT image data records X1 and X2 by cross-hatching, wherein the voxel V(r±Δr) which at least at certain points is immediately adjacent, is provided with diagonal hatching. For the correlation calculation in the form of a regression analysis and determination of the gradient of the regression line as correlation coefficient ki, the spatially identical voxels of both the CT image data records are referred to in each case. This is indicated in the representation by the broken connecting lines between three voxels in each case.

Although the representation shown here represents only a section plane in the CT image data records and their spatial correlation, this two-dimensional consideration can also be extended to a third dimension, perpendicular to the image plane.

Figure 3:
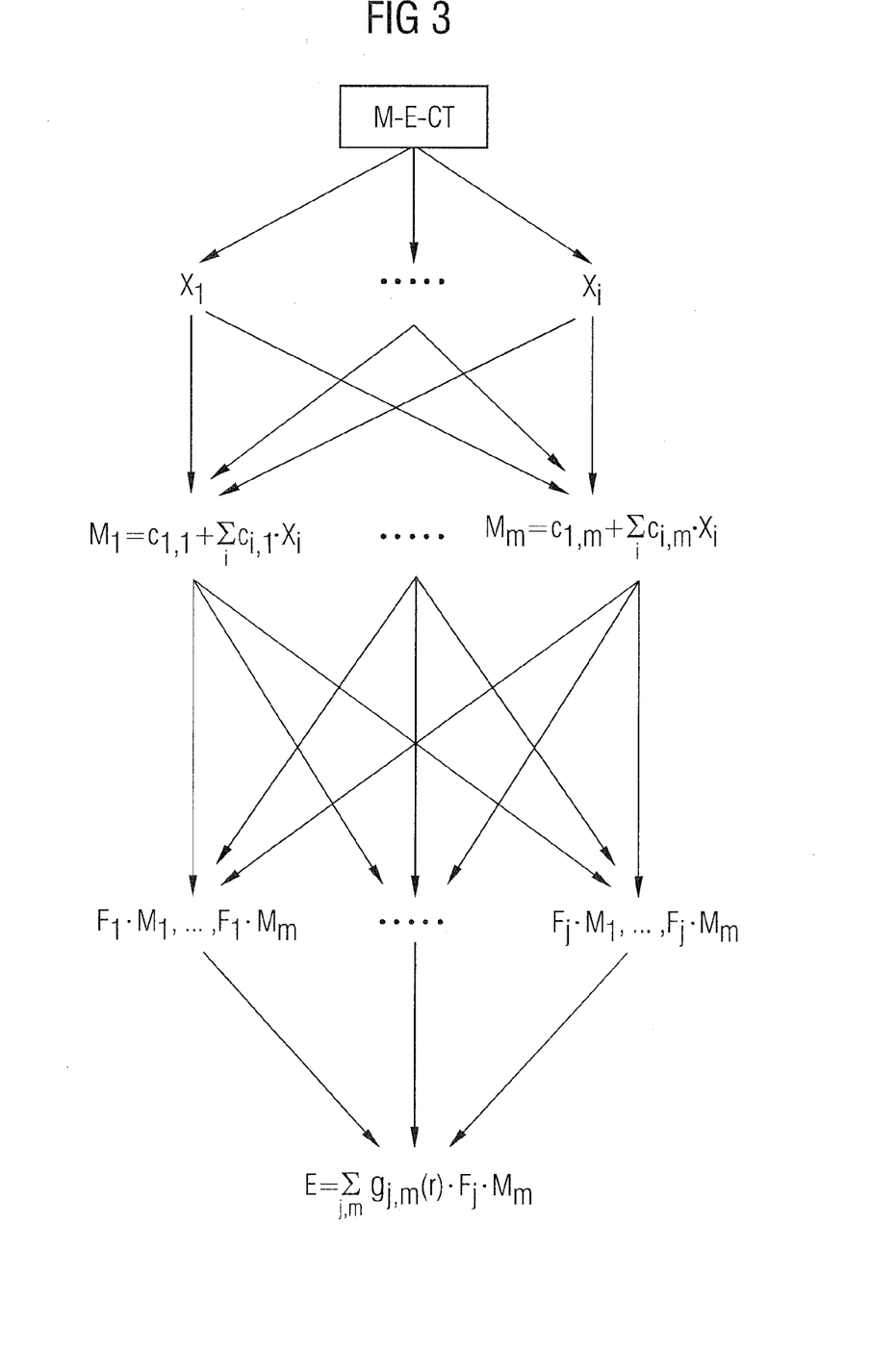
FIG. 3: Diagrammatic representation of the method according to an embodiment of the invention.

A diagrammatic representation of the method according to an embodiment of the invention is shown, for example, in FIG. 3. On the basis of this, several CT image data records Xi are produced with a M(ulti)-E(nergy) C(omputer) T(omography system). From this, mixed image data records $$M_m = c_{0,m} + \sum_i c_{i,m} \cdot X_i$$

are formed, which are then broken down, by the use of different filter operators Fj in each case into different frequency bands. Finally, a result image E is calculated, in that mixed image data records $F_j \cdot M_m$, broken down into frequency bands, are multiplied and totaled, with the use of a location-dependent function $g_{j,m}(r)$ with $$E = \sum_{j,m} g_{j,m}(r) \cdot F_j \cdot M_m,$$

wherein $g_{0,0}(r)=1$.

Figure 4:
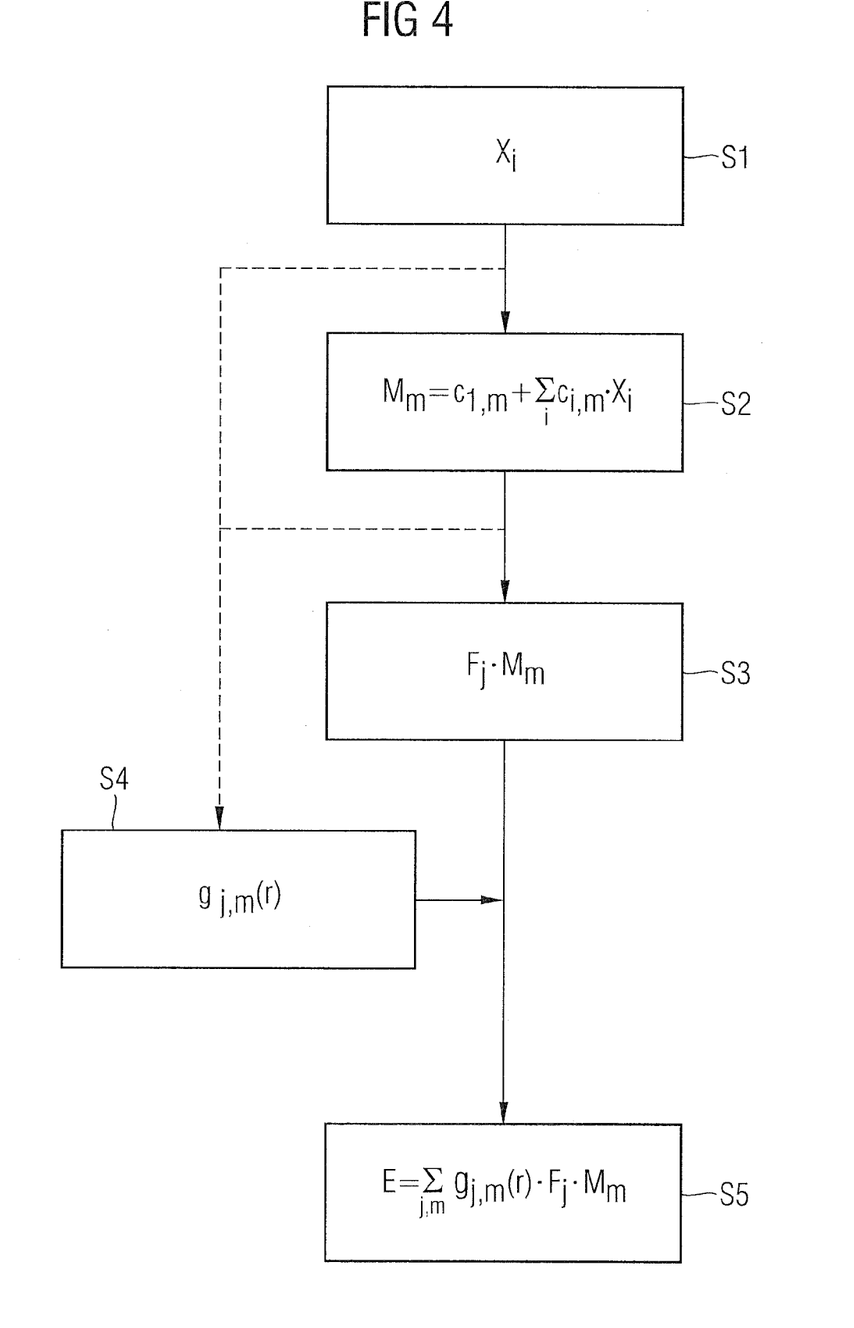
FIG. 4: Alternative representation of the method sequence.

A corresponding method diagram is shown in FIG. 4. In the method step S1, the CT image data records Xi are determined, from which, in the method step S2, mixed image data records with $$M_m = c_{0,m} + \sum_i c_{i,m} \cdot X_i$$

are formed. This is followed in method step S3 by the breakdown of the mixed image data records into different frequency bands with $F_j \cdot M_m$. In addition, in an independent method step S4, from correlation considerations, threshold value considerations, or findings from a material breakdown with the aid of the CT image data records Xi or mixed image data records Mm, the location-dependent function $g_{j,m}(r)$ is determined in such a way that, in the method step S5, by weighted totaling of the mixed images broken down into frequency bands with the location-dependent function, a result image according to $$E = \sum_{j,m} g_{j,m}(r) \cdot F_j \cdot M_m$$

is calculated.

Overall, therefore, with an embodiment of the invention a method is proposed for the production of a noise-reduced CT image data record by frequency band breakdown, a computer system for carrying out the method, and a CT system with such a computer system, wherein, from several simultaneously-recorded energy spectrum-specific CT image data records $X_i$ several linear-combined mixed image data records $$M_m = c_{0,m} + \sum_i c_{i,m} \cdot X_i$$

are produced, a frequency band breakdown of the mixed image data records $M_m$ into a first lowest frequency band $F_0$ and several higher frequency bands takes place, and a result image data record $$E = \sum_{j,m} g_{j,m}(r) \cdot F_j \cdot M_m$$

is calculated, in that each mixed image data record $M_m$ is multiplied by precisely one filter and one location-dependent function $g_{j,m}(r)$ and totaled, wherein $g_{0,0}(r)=1$.

Although the invention has been illustrated and described in greater detail by the example embodiment, the invention is not restricted by the examples disclosed, and other variations can be derived from these by a person skilled in the art, without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing a result image data record, the method comprising:

simultaneously recording a plurality of energy spectrum-specific CT image data records ($X_i$) with different X-ray energy spectra ($R_i$) or received from a plurality of simultaneously-recorded energy spectrum-specific CT image data records ($X_i$) with different X-ray energy spectra ($R_i$);

calculating a plurality of linear mixed image data records $$\left(M_m = c_{0,m} + \sum_i c_{i,m} \cdot X_i\right),$$

mixed from the energy spectrum-specific CT image data records ($X_i$);

breaking down, via frequency band breakdown, the mixed image data records ($M_m$) into a first relatively lowest frequency band produced with a low-pass filter ($F_0$) and a plurality of relatively higher frequency bands produced by other filters ($F_j$), wherein all the other filters ($F_j$, j≠0) block a frequency zero and wherein a sum over all the filters for all frequencies (f) is standardized $$\left(\sum_j F_j(f) = 1\right);$$

and calculating the result image data record $$\left(E = \sum_{j,m} g_{j,m}(r) \cdot F_j \cdot M_m\right),$$

in which each mixed image data record ($M_m$) is multiplied by precisely one of the filters and by one location-dependent function ($g_{j,m}(r)$) and is totaled, wherein $g_{0,0}(r)=1$.

2. The method of claim 1, wherein the location-dependent function ($g_{j,m}(r)$) is arranged such that local areas of the skin surface exhibit a constant value which is different from inner regions of the patient.

3. The method of claim 1, wherein the location-dependent function ($g_{j,m}(r)$) is determined locally from a statistical evaluation of the surroundings of each voxel ($V(r)$) at the location (r).

4. The method of claim 3, wherein the statistical evaluation includes:

selecting a CT image data record ($X_1$);

calculating regression coefficients ($k_i$=gradient of the regression lines) from the CT image data record ($X_1$), moving over adjacent voxels ($V(r\pm\Delta r)$) of every voxel considered ($V(r)$), to the remaining CT image data records ($X_i$), which indicate the mutual dependency of the CT values of the adjacent voxel ($V(r\pm\Delta r)$) in each case of the CT image data records ($X_i$) to the selected CT image data record ($X_1$), determining a location-dependent scaling function $$\left(h_m(r) = \frac{\sum_i c_{i,0} k_i}{\sum_i c_{i,m} k_i}\right);$$

determining, from the location-dependent scaling function, the location-dependent function ($g_{j,m}(r)=w_{j,m}(r) \cdot h_m(r)$), wherein $$\sum_m w_{j,m} = 1$$

is for all j; and determining the result image data record $$\left(E = \sum_{j,m} g_{j,m}(r) \cdot F_j \cdot M_m\right)$$

as a totaling of a product from the location-dependent function with the filters and the mixed images.

5. The method of claim 1, wherein the location-dependent function ($g_{j,m}(r)$) is determined by a classification on the basis of the local CT values.

6. The method of claim 1, wherein the location-dependent function ($g_{j,m}(r)$) is determined by a classification of locally-determined materials.

7. The method of claim 1, wherein the local materials are determined by a material breakdown of the CT image data records ($X_i$) into at least two materials.

8. The method of claim 1, wherein the energy spectrum-specific CT image data records ($X_i$) are two-dimensional section image data records.

9. The method of claim 1, wherein the energy spectrum-specific CT image data records ($X_i$) are three dimensional volume image data records.

10. The method of claim 1, wherein, as energy-specific CT image data records ($X_i$), two CT image data records ($X_i$) of a dual-energy CT scan are used.

11. The method of claim 1, wherein the respective CT image data records ($X_i$) derive from or correspond to a scanning with a mono-energetic X-ray spectrum.

12. The method of claim 1, wherein the respective CT image data records ($X_i$) correspond to a scanning with a mono-energetic X-ray spectrum.

13. A computer system, comprising:
a memory, configured to store a computer program which is to be executed during operation of the computer system, the computer program carrying out the method of claim 1 when executed.

14. A CT system for producing several linear mixed image data records $$\left(M_m = c_{0,m} + \sum_i c_{i,m} \cdot X_i\right)$$

mixed from the energy spectrum-specific CT image data records ($X_i$), comprising the computer system of claim 13.

15. The method of claim 8, wherein, as energy-specific CT image data records ($X_i$), two CT image data records ($X_i$) of a dual-energy CT scan are used.

16. The method of claim 9, wherein, as energy-specific CT image data records ($X_i$), two CT image data records ($X_i$) of a dual-energy CT scan are used.

17. A non-transitory computer readable medium including computer program product, the computer program product comprising instructions, which when executed by a processor, cause the processor to perform the function of claim 1.

* * * * *